Figure 1:
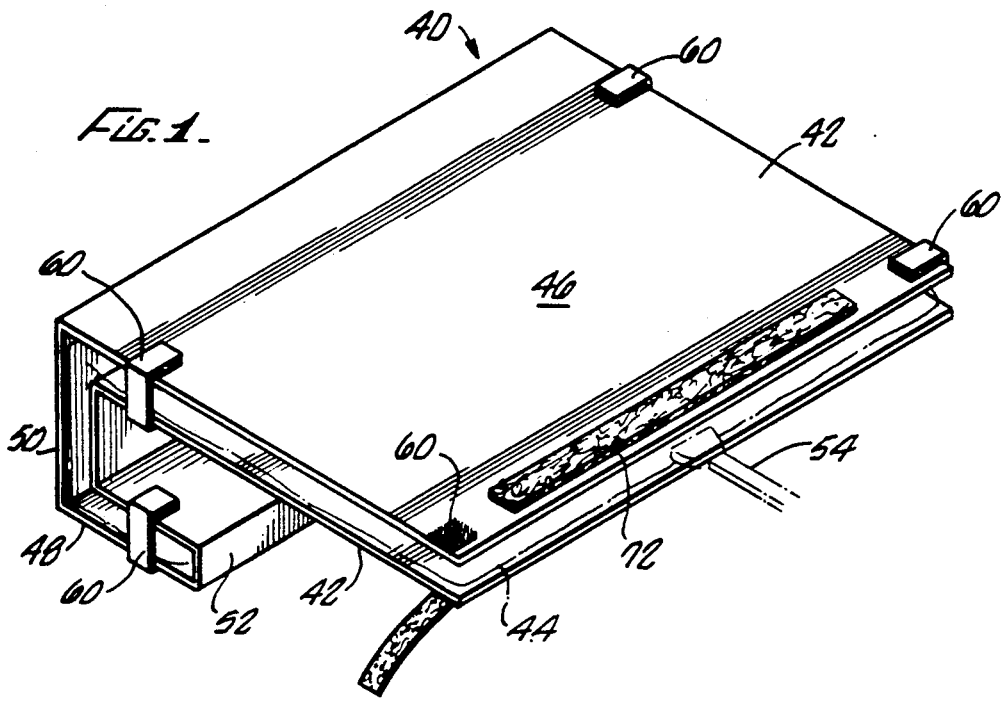

United States Patent [19]
Klawitter et al.

[11] Patent Number: 5,081,657
[45] Date of Patent: Jan. 14, 1992

[54] BUCKY WARMER

[75] Inventors: Hartmut Klawitter, Santee; Louise C. Miller, Descanso, both of Calif.

[73] Assignee: National Imaging Consultants, Inc., Santee, Calif.

[21] Appl. No.: 611,303

[22] Filed: Nov. 9, 1990

[51] Int. Cl.⁵ .......................... A61B 6/04; H05B 1/00
[52] U.S. Cl. ........................ 378/37; 378/177; 378/208; 378/210; 219/217; 219/528; 128/403
[58] Field of Search .............. 378/37, 208, 177, 180, 378/210; 128/399, 403, 402; 219/217, 218, 528

[56] References Cited
U.S. PATENT DOCUMENTS 4,868,898  9/1989  Sato ........................ 128/403
4,937,435  6/1990  Goss et al. .................. 219/528

Primary Examiner—Edward P. Westin
Assistant Examiner—Don Wong
Attorney, Agent, or Firm—Jeffrey G. Sheldon

[57] ABSTRACT

A device for warming at least a portion of the top surface of a bucky table of a mammography machine is provided. The device has two substantially parallel, spaced apart, heat-conductive plates adapted to be removably placed onto the table. A heating pad is placed between the two plates for warming at least a portion of the upper surface of the table. Means are provided for releasably holding the plates together so that the heating pad can be placed between the plates and removed therefrom.

17 Claims, 1 Drawing Sheet

BUCKY WARMER

BACKGROUND

Mammography is a medical procedure that is becoming more and more common due to increased incidence of breast cancer in women. It is estimated that in the United States about 31 percent of women over 40 have a mammogram performed every year or two. In a typical mammography procedure, the patient places her breasts on a table that holds the x-ray film, commonly referred to as a "bucky" table, and then an upper panel is lowered against the top of the woman's breasts, thereby sandwiching the breasts in between the table and the panel. After x-rays are taken, the woman's breasts are released.

A common complaint of women undergoing mammography is that the plates are cold, generally being at room temperature, and thus serving as a heat sink.

In view of these complaints, courteous operators have attempted to maintain the bucky warm by placing an electric heating pad on the bucky, and holding the pad in position with rubber bands, wires, or the like. However, this is a cumbersome solution, requiring substantial time, and many operators do not go to the trouble of maintaining the bucky warm. Moreover, when the heating pad is not in use, there is no convenient place to store it, and it often becomes soiled.

Therefore, there is a need for a device that easily and inexpensively maintains surfaces with which women come into contact during a mammography procedure warm and comfortable.

SUMMARY

The present invention provides a device that satisfies this need. In its simplest form, the device comprises two substantially parallel, spaced apart, heat-conductive plates. There is a removable heating unit between the two plates for warming the bucky. The heating means can be a heating pad. The device includes means for releasably holding the plates together, such as a hook and loop fastener. The device can be removably placed onto the bucky table of the mammography machine.

In a preferred version of the invention, the plates are joined together at one end thereof, and are formed of a sufficiently flexible material, such as polycarbonate plastic, that the plates can be spread apart for putting a heating pad therebetween.

It is also preferred that the device be provided with hanging means that cooperates with a hanging mechanism mounted on the mammography machine so that the heating device, when not being used, can be stored on the mammography machine in a convenient location.

In a preferred version of the invention, the two heat-conductive plates have a generally J-shaped configuration, each plate comprising a first elongated segment sized to fit on the upper surface of the bucky, and a second segment substantially parallel to the first segment and shorter than the first segment, the second segment being sized to fit on the bottom surface of the bucky. There is an intermediate segment joining the first and second segments which is sized to fit over the peripheral edge of the bucky. This allows the device to be removably placed on the bucky table.

It is also preferred that the distance between the first and second segment decreases away from the intermediate segment, i.e., the first and second segments are tapered inwardly toward each other, so that the device snugly fits onto the table. This is one advantage of having a J-shaped configuration. Another advantage of a J-shaped configuration is that the second shorter segment warms the underside of the table, which is important for a relatively obese woman, who can have bare flesh contact with the underside of the bucky table.

DRAWINGS

Figure 2:
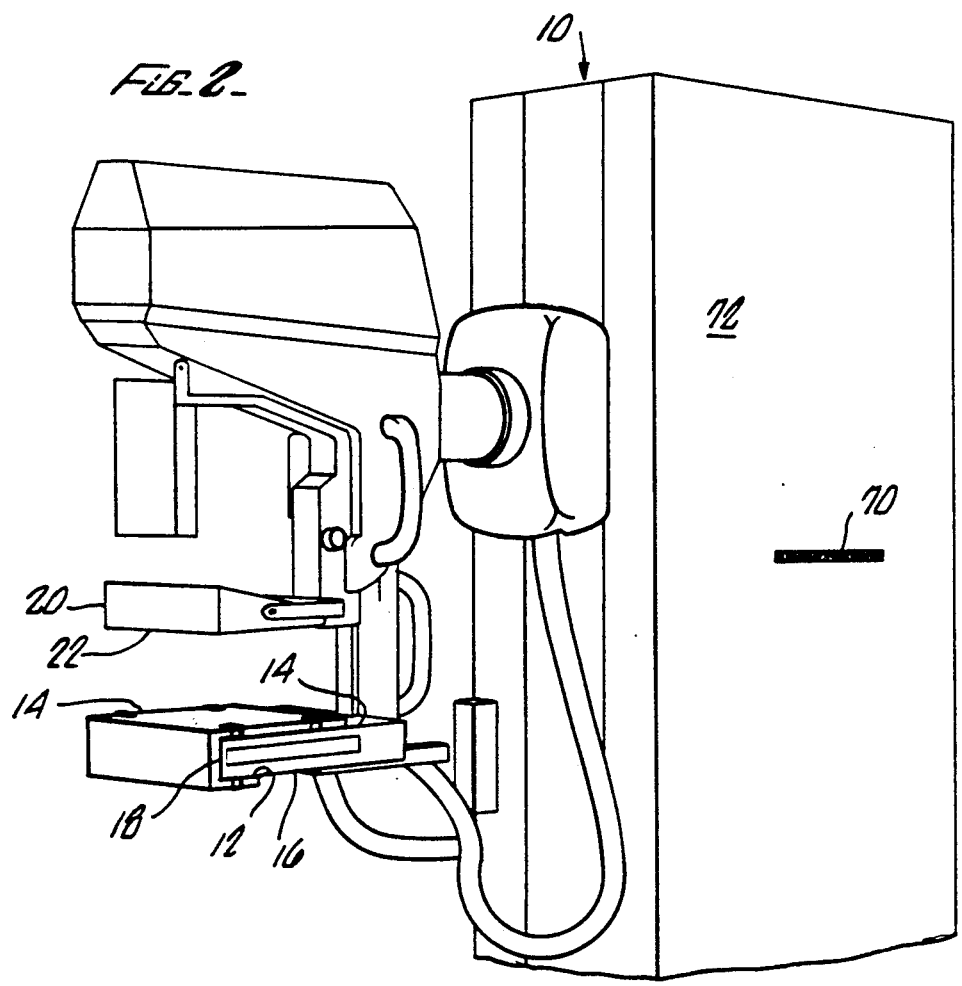

These and other features, aspects and advantages of the present invention will become better understood from the following description, appended claims, and accompanying drawings where:

FIG. 1 is a perspective view of the device embodying features of the present invention; and FIG. 2 shows the device of FIG. 1 mounted on a bucky of a mammography machine.

DESCRIPTION

With preference to the drawings, a mammography machine 10 has a bucky plate 12 that receives x-ray film. The plate 12 has a top surface 14 on which a woman places her breasts, a bottom surface 16, and a peripheral edge 18. Above the bucky table 12 is a panel 20 or similar structure that can be lowered onto the top surface 14 of the bucky. The panel 20 has a lower surface 22.

With reference to FIG. 1, a device 40 for warming the bucky comprises two substantially identical, parallel, spaced apart, heat-conductive plates 42 having a heating pad 44 sandwiched therebetween. The plates have a generally J-shaped configuration, each comprising a first elongated segment 46, a second segment 48 substantially shorter than the first segment 46 and generally parallel thereto, and an intermediate segment 50 joining the first segment 46 and the second segment 48.

Preferably the plates are formed from a substantially transparent material so that the heating pad can be seen. The preferred material for forming the plates is a polycarbonate plastic having a thickness of about 0.060 inch.

In a preferred version of the invention, the second segments 48 of the two plates 42 are joined together at their distal ends by a rib 52. Thus, the two plates can be formed from a single sheet of plastic material bent to form two generally J-shaped plates connected to each other.

The plates 42 are formed of a sufficiently flexible material that they can be pried apart for receiving the heating pad 44. Thus, the heating pad can be placed between the plates and removed from the plates as needed, such as for cleaning or replacing the heating pad. The heating pad 44 has a conventional electrical cord 54 for connection into an outlet (not shown) and can be provided with a thermostatic control (not shown).

Preferably the device 40 includes means for releasably holding the plates together so that the heating pad is snugly held in between the plates. As shown in the drawings, the holding means can be Velcro brand hook and loop fasteners 60 positioned at the peripheral edge of the plates at selected locations. In the version of the invention shown in FIG. 1, six such hook and loop fasteners are provided with one half of the fastener device attached to one of the plates and the other half of the fastener device attached to the other plate.

As shown by FIG. 2, the size of the first segments of the plates, both in width and length, is sufficiently large to cover a substantial portion of the upper surface 14 of the bucky 12. The size and configuration of the second segment 48 of each plate is adapted to cover a portion of the bottom surface 16 of the bucky 12. The intermediate segment 50 is sized to fit over the peripheral edge 18 between the top surface 14 and the bottom surface 16 of the bucky 12.

Preferably the distance between the first segment 46 and the segment 48 decreases away from the intermediate segment 50, i.e., the first and second segments taper inwardly towards each other. This allows the device 40 to snugly fit onto the bucky table.

A problem with prior art heating pads used for warming a bucky is what to do with them when they are not used. This problem has been solved by the present invention by providing a fastener system so that the device 40 can be hung on the side of the machine 10. For example, as shown in FIG. 2, a hook and loop fastener system is used. The hook portion 70 can be mounted on a side wall 72 of the mammography machine 12, and the loop fastener portion 72 can be placed on the first segment 46 of one of the plates 42, or vice versa. Thus, when the device 40 is not in use, it can be hung on the side wall 72 of the mammography device 10.

Although the present invention has been described in considerable detail with reference to certain preferred versions thereof, other versions are possible. For example, an electrical heating pad 44 not be used. Heating means such as a hot water bottle can be used. Moreover, plastic materials other as polycarbonate, such as polyvinylchloride can be provided. Moreover, the polycarbonate can be filled with a heat conductive metal or other material to improve its heat conduction properties. Moreover, in some mammography machines, the table on which a woman places her breasts does not contain x-ray film. Thus the device 40 can be used for heating surfaces other than those which contain x-ray film.

Therefore, the scope of the appended claims should not be limited to the description of the preferred versions contained herein.

What is claimed is:

1. In a mammography machine having a table on which the breasts to be X-rayed are placed and a panel that sandwiches the breast against the table, the table having an upper surface on which the breasts are placed, a peripheral edge, and a bottom surface, the panel have a bottom surface by which the breasts are sandwiched, the improvement comprising a removable device for warming surfaces of the mammography machine that a patient contacts, the device comprising:
   a) two substantially parallel, spaced apart, heat-conductive plates having a generally J-shaped configuration, each plate comprising a first elongated segment sized to fit on the upper surface of the table, a second segment substantially parallel to the first segment and shorter than the first segment, the second segment being sized to fit on the bottom surface of the table, and an intermediate segment joining the first and second segments and sized to fit over the peripheral edge of the table, wherein the device is adapted to be removably placed onto the table;
   b) a heating pad sandwiched between the two plates for warming portions of the upper surface of the table, the bottom surface of the table, the peripheral edge of the table, and the bottom surface of the panel when the device is placed on the table and the panel is placed proximate to the table; and
   c) means for releasably holding the plates together so that the heating pad can be placed between the plates and removed therefrom.

2. The machine of claim 1 wherein the means for releasably holding the plates together comprises a hook and loop fastener means.

3. The machine of claim 1 in which the plates are joined together at the end of the second segments.

4. The machine of claim 1 wherein the device includes means for attaching the device to the machine in a storage position.

5. The machine of claim 3, wherein the plates are formed from a sufficiently flexible material that they can be pried apart for receiving the heating pad.

6. The machine of claim 5 wherein the plates are formed from polycarbonate.

7. The machine of claim 1 wherein the plates are formed from a substantially transparent material.

8. A removable device for warming at least a portion of the top surface of a table of a mammography machine, the table being one upon which a patient places her breasts, the table having a peripheral edge and a bottom surface, the device comprising:
   a) two substantially parallel, spaced apart, heat-conductive plates removably placabile onto the table;
   b) removable heating means between the two plates for warming at least a portion of the upper surface of the table; and
   c) means for releasably holding the plates together so that the heating means can be placed between the plates and removed therefrom.

9. The device of claim 8 wherein each plate has a generally J-shaped configuration, each plate comprising a first elongated segment sized to fit on the upper surface of the table, a second segment substantially parallel to the first segment and shorter than the first segment, the second segment being sized to fit on the bottom surface of the table, and an intermediate segment joining the first and second segments and sized to fit over the peripheral edge of the table.

10. The device of claim 8 in which the heating means is a heating pad.

11. The device of claim 8 wherein the means for releasably holding the plates together comprises a hook and loop fastener means.

12. The device of claim 9 in which the plates are joined together at the end of the second segments.

13. The device of claim 11 wherein the device includes means for attaching the device to the machine in a storage position.

14. The device of claim 12, wherein the plates are formed from a sufficiently flexible material that they can be pried apart for receiving the heating pad.

15. The device of claim 14 wherein the plates are formed from polycarbonate.

16. The machine of claim 8 wherein the plates are formed from a substantially transparent material.

17. The device of claim 9 wherein the first and second segments taper inwardly towards each other away from the intermediate segment so that the device can rest snugly onto the table.

* * * * *